(12) United States Patent
Charrier et al.

(10) Patent No.: US 7,691,885 B2
(45) Date of Patent: Apr. 6, 2010

(54) PYRIDONES USEFUL AS INHIBITORS OF KINASES

(75) Inventors: Jean-Damien Charrier, Wantage (GB); Sharn Ramaya, Burghfield Common (GB); Steven Durrant, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 844 days.

(21) Appl. No.: 11/511,895

(22) Filed: Aug. 29, 2006

(65) Prior Publication Data

US 2007/0155794 A1    Jul. 5, 2007

Related U.S. Application Data

(60) Provisional application No. 60/712,642, filed on Aug. 29, 2005.

(51) Int. Cl.
*A61K 31/4439* (2006.01)
*C07D 403/04* (2006.01)

(52) U.S. Cl. .................. 514/338; 514/339; 514/340; 546/273.4; 546/275.4; 546/275.7; 546/277.4; 546/268.4; 546/276.4

(58) Field of Classification Search .................. None
See application file for complete search history.

(56) References Cited

U.S. PATENT DOCUMENTS

| | | | |
|---|---|---|---|
| 5,290,941 | A | 3/1994 | Volante et al. |
| 5,308,854 | A | 5/1994 | Hoffman, Jr. et al. |
| 5,356,911 | A | 10/1994 | Muller-Gliemann et al. |
| 5,399,566 | A | 3/1995 | Katano et al. |
| 5,407,948 | A | 4/1995 | Fey et al. |
| 5,414,003 | A | 5/1995 | Fey et al. |
| 5,492,923 | A | 2/1996 | Fey et al. |
| 5,599,823 | A | 2/1997 | Muller-Gliemann et al. |
| 5,712,296 | A | 1/1998 | Fey et al. |
| 6,774,138 | B2 | 8/2004 | Cosford et al. |
| 7,524,967 | B2 | 4/2009 | Koyakumaru et al. |
| 2003/0187026 | A1 | 10/2003 | Li et al. |
| 2003/0199511 | A1 | 10/2003 | Li et al. |
| 2003/0220368 | A1 | 11/2003 | Ozaki et al. |
| 2004/0023973 | A1 | 2/2004 | Nagato et al. |
| 2006/0004205 | A1 | 1/2006 | Koyakumaru et al. |
| 2007/0179156 | A1 | 8/2007 | Charrier et al. |
| 2007/0185125 | A1 | 8/2007 | Charrier et al. |

FOREIGN PATENT DOCUMENTS

| | | |
|---|---|---|
| EP | 0462800 A2 | 6/1991 |
| EP | 0481802 A1 | 10/1991 |
| EP | 0623611 A1 | 4/1994 |
| EP | 1300396 A1 | 4/2003 |
| WO | 9119697 A1 | 12/1991 |
| WO | 9955676 A1 | 11/1999 |
| WO | 0196308 A1 | 12/2001 |
| WO | 0240448 A1 | 5/2002 |
| WO | 02053543 A1 | 7/2002 |
| WO | 02079192 A1 | 10/2002 |
| WO | 03047577 A2 | 6/2003 |
| WO | 03051366 A2 | 6/2003 |
| WO | 03068230 A1 | 8/2003 |
| WO | 2004031151 A1 | 4/2004 |
| WO | 2004035563 A1 | 4/2004 |
| WO | 2004035564 A1 | 4/2004 |
| WO | 2004050657 A2 | 6/2004 |
| WO | 2004058726 A2 | 7/2004 |
| WO | 2005007159 A1 | 1/2005 |
| WO | 2005097750 A1 | 10/2005 |
| WO | 2006017443 A1 | 2/2006 |
| WO | 2006065946 A1 | 6/2006 |
| WO | 2006099075 A2 | 9/2006 |

OTHER PUBLICATIONS

International Search Report for corresponding PCT Application No. PCT/US2006/033510 filed on Aug. 29, 2006.

*Primary Examiner*—Zinna N Davis
(74) *Attorney, Agent, or Firm*—Jennifer G. Che

(57) ABSTRACT

The present invention relates to compounds useful as inhibitors of protein kinase. The invention also provides pharmaceutically acceptable compositions comprising said compounds and methods of using the compositions in the treatment of various disease, conditions, or disorders. The invention also provides processes for preparing compounds of the inventions.

27 Claims, No Drawings

PYRIDONES USEFUL AS INHIBITORS OF KINASES

CROSS REFERENCE TO RELATED APPLICATIONS

This present application claims the benefit, under 35 U.S.C. §119, to U.S. Provisional Application No. 60/712,642, filed Aug. 29, 2005; the entire disclosure of which is incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders. The invention also provides processes for preparing the compounds of the invention.

BACKGROUND OF THE INVENTION

The Tec family of non-receptor tyrosine kinases plays a central role in signaling through antigen-receptors such as the TCR, BCR and Fcε receptors (reviewed in Miller A, et al. Current Opinion in Immunology 14; 331-340 (2002). Tec family kinases are essential for T cell activation. Three members of the Tec family, Itk, Rlk and Tec, are activated downstream of antigen receptor engagement in T cells and transmit signals to downstream effectors, including PLC-γ. Deletion of Itk in mice results in reduced T cell receptor (TCR)-induced proliferation and secretion of the cytokines IL-2, IL-4, IL-5, IL-10 and IFN-γ. (Schaeffer et al, Science 284; 638-641 (1999)), Fowell et al, Immunity 11; 399-409 (1999), Schaeffer et al Nature Immunology 2, 12; 1183-1188 (2001))). The immunological symptoms of allergic asthma are attenuated in Itk−/− mice. Lung inflammation, eosinophil infiltration and mucous production are drastically reduced in Itk−/− mice in response to challenge with the allergen OVA (Mueller et al, Journal of Immunology 170: 5056-5063 (2003)). Itk has also been implicated in atopic dermatitis. This gene has been reported to be more highly expressed in peripheral blood T cells from patients with moderate and/or severe atopic dermatitis than in controls or patients with mild atopic dermatitis (Matsumoto et al, International archives of Allergy and Immunology 129; 327-340 (2002)).

Tec family kinases are also essential for B cell development and activation. Patients with mutations in Btk have a profound block in B cell development, resulting in the almost complete absence of B lymphocytes and plasma cells, severely reduced Ig levels and a profound inhibition of humoral response to recall antigens (reviewed in Vihinen et al Frontiers in Bioscience 5:d917-928).

Tec kinases also play a role in mast cell activation through the high-affinity IgE receptor (FcεRI). Itk and Btk are expressed in mast cells and are activated by FcεRI cross-linking (Kawakami et al, Journal of Immunology; 3556-3562 (1995)). Btk deficient murine mast cells have reduced degranulation and decreased production of proinflammatory cytokines following FcεRI cross-linking (Kawakami et al. Journal of leukocyte biology 65:286-290). Btk deficiency also results in a decrease of macrophage effector functions (Mukhopadhyay et al, Journal of Immunology; 168, 2914-2921 (2002)).

Accordingly, there is a great need to develop compounds useful as inhibitors of protein kinases. In particular, it would be desirable to develop compounds that are useful as inhibitors of Tec family (e.g., Tec, Btk, Itk/Emt/Tsk, Bmx, Txk/Rlk) protein kinases.

SUMMARY OF THE INVENTION

This invention relates to compounds and compositions useful as protein kinase inhibitors. Compounds of this invention, and pharmaceutically acceptable compositions thereof, are effective as inhibitors of protein kinases. In certain embodiments, these compounds are effective as inhibitors of Tec family (e.g., Tec, Btk, Itk/Emt/Tsk, Bmx, Txk/Rlk) protein kinases. These compounds have the formula I, as defined herein, or a pharmaceutically acceptable salt thereof.

These compounds and pharmaceutically acceptable compositions thereof are useful for treating or preventing a variety of diseases, disorders or conditions, including, but not limited to, an autoimmune, inflammatory, proliferative, or hyperproliferative disease or an immunologically-mediated disease. The compounds and compositions are also useful in methods for preventing thrombin-induced platelet aggregation. The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

1. General Description of Compounds of the Invention

This invention provides compounds of Formula I:

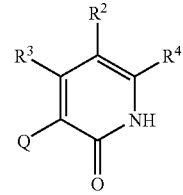

Formula I or a pharmaceutically accepted salt thereof, wherein
  $R^2$ is a 3-8-membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring having 0-5 heteroatoms independently selected from nitrogen, oxygen, or sulfur; wherein $R^2$ is optionally substituted with 0-5 $J^{R2}$;
  each $R^3$ and $R^4$ is independently H, halogen, or $C_{1-4}$ aliphatic optionally substituted with 0-5 occurrences of halogen, OH, $OCH_3$, $OCF_3$, $NO_2$, $NH_2$, CN, $NHCH_3$, $SCH_3$, $N(CH_3)_2$, or $C_{1-2}$ aliphatic optionally substituted 0-5 times with F; this definition of $R^3$ and $R^4$ includes perfluorinated methyl and ethyl;
  Q is 5-membered heteroaryl containing 1-4 nitrogen atoms, wherein one of the nitrogen atoms is NH; each Q is optionally substituted with 0-3 $J^Q$ and is optionally fused to ring $Q^1$;
  $Q^1$ is a 5-6 membered aryl or heteroaryl ring containing up to 3 heteroatoms selected from O, N, and S; each $Q^1$ is optionally substituted with 0-5 $J^Q$;

$J^{R2}$ and $J^Q$ are each independently halogen, —NO$_2$, —CN, C$_{1-6}$ aliphatic, C$_{6-10}$aryl, —C$_{1-6}$alkyl-(C$_{6-10}$aryl), 5-12 membered heteroaryl, —C$_{1-6}$alkyl-(5-12 membered heteroaryl), 3-12 membered heterocyclyl, —C$_{1-6}$alkyl-(3-12 membered heterocyclyl), C$_{3-10}$cycloaliphatic, —C$_{1-6}$ alkyl-(C$_{3-10}$cycloaliphatic), —OR$^\circ$, —SR$^\circ$, —N(R$^\circ$)$_2$, —(C$_{1-6}$alkyl)-OR$^\circ$, —(C$_{1-6}$alkyl)-N(R$^\circ$)$_2$, —(C$_{1-6}$alkyl)-SR$^\circ$, —NR$^\circ$C(O)R$^\circ$, —NR$^\circ$C(S)R$^\circ$, —NR$^\circ$C(O)N(R$^\circ$)$_2$, —NR$^\circ$C(S)N(R$^\circ$)$_2$, —NR$^\circ$CO$_2$R$^\circ$, —NR$^\circ$NR$^\circ$C(O)R$^\circ$, —NR$^\circ$NR$^\circ$C(O)N(R$^\circ$)$_2$, —NR$^\circ$NR$^\circ$CO$_2$R$^\circ$, —C(O)C(O)R$^\circ$, —C(O)CH$_2$C(O)R$^\circ$, —CO$_2$R$^\circ$, —C(O)R$^\circ$, —C(S)R$^\circ$, —C(O)N(R$^\circ$)$_2$, —C(S)N(R$^\circ$)$_2$, —OC(O)N(R$^\circ$)$_2$, —OC(O)R$^\circ$, —C(O)N(OR$^\circ$)R$^\circ$, —C(NOR$^\circ$)R$^\circ$, —S(O)$_2$R$^\circ$, —S(O)$_3$R$^\circ$, —SO$_2$N(R$^\circ$)$_2$, —S(O)R$^\circ$, —NR$^\circ$SO$_2$N(R$^\circ$)$_2$, —NR$^\circ$SO$_2$R$^\circ$, —N(OR$^\circ$)R$^\circ$, —C(=NH)—N(R$^\circ$)$_2$, —P(O)$_2$R$^\circ$, —PO(R$^\circ$)$_2$, —OPO(R$^\circ$)$_2$, =O, =S, =NNHR$^\circ$, =NN(R$^\circ$)$_2$, =NNHC(O)R$^\circ$, =NNHCO$_2$(C$_{1-6}$alkyl), =NNHSO$_2$(C$_{1-6}$alkyl), =NOH, =NR$^\circ$; or C$_{1-10}$ alkylidene chain, wherein up to three methylene units of the chain are independently replaced by —NR$^\circ$—, —O—, —S—, —SO—, SO$_2$—, or —CO—; wherein each $J^{R2}$ and $J^Q$ is independently and optionally substituted with 0-5 R$^X$;

each R$^X$ is independently H, halogen, NO$_2$, CN, NH$_2$, NH(C$_{1-4}$aliphatic), N(C$_{1-4}$aliphatic)$_2$, OH, O(C$_{1-4}$aliphatic), O(C$_{1-4}$haloaliphatic), CO(C$_{1-4}$aliphatic), CO$_2$H, CO$_2$(C$_{1-4}$aliphatic), C$_{1-6}$aliphatic, C$_{1-4}$haloaliphatic, phenyl, —O(Ph), 5-6 membered heteroaryl, C$_{3-8}$cycloaliphatic, 5-8 membered heterocyclyl, —C$_{1-6}$ aliphatic-(Ph), —C$_{1-6}$alkyl-(5-6 membered heteroaryl), —C$_{1-6}$alkyl-(C$_{3-8}$cycloaliphatic), —C$_{1-6}$alkyl-(5-8 membered heterocyclyl), or C$_{1-10}$alkylidene chain wherein up to 2 methylene units of the chain are optionally replaced by O, N, or S; wherein each R$^X$ and is independently and optionally substituted with 0-5 J$^\circ$;

each R$^\circ$ is independently H, C$_{1-6}$aliphatic, C$_{1-4}$haloaliphatic, CO(C$_{1-4}$aliphatic), CO$_2$(C$_{1-4}$aliphatic), —SO$_2$(C$_{1-4}$aliphatic), —SO$_2$(phenyl), phenyl, 5-6 membered heteroaryl, 5-8 membered heterocyclyl, C$_{3-8}$cycloaliphatic, —C$_{1-6}$aliphatic-(Ph), —C$_{1-6}$alkyl-(5-6 membered heteroaryl), —C$_{1-6}$alkyl-(5-8 membered heterocyclyl), —C$_{1-6}$alkyl-(C$_{3-8}$cycloaliphatic); or C$_{1-10}$alkylidene chain wherein up to 2 methylene units of the chain are optionally replaced by O, N, or S; wherein said R$^\circ$ is optionally substituted with 0-6 J$^\circ$;

or two R$^\circ$, on the same substituent or different substituents, taken together with the atom(s) to which each R$^\circ$ group is bound, form a 3-8 membered saturated, partially unsaturated, or fully unsaturated monocyclic or bicyclic ring having 0-4 heteroatoms independently selected from nitrogen, oxygen, or sulfur; wherein said ring is optionally and independently substituted with 0-4 occurrences of halogen, NO$_2$, CN, C$_{1-4}$aliphatic, NH$_2$, NH(C$_{1-4}$aliphatic), N(C$_{1-4}$aliphatic)$_2$, OH, O(C$_{1-4}$aliphatic), CO$_2$H, CO$_2$(C$_{1-4}$aliphatic), O(haloC$_{1-4}$ aliphatic), or haloC$_{1-4}$aliphatic, wherein each of the R$^\circ$ C$_{1-4}$aliphatic groups is unsubstituted;

each J$^\circ$ is independently halogen, NO$_2$, CN, C$_{1-4}$ aliphatic, —NH$_2$, —NH(C$_{1-4}$ aliphatic), —N(C$_{1-4}$ aliphatic)$_2$, —OH, —O(C$_{1-4}$ aliphatic), —CO$_2$H, —CO$_2$(C$_{1-4}$ aliphatic), —O(haloC$_{1-4}$ aliphatic), and haloC$_{1-4}$ aliphatic), wherein each of the J$^\circ$ C$_{1-4}$aliphatic groups is unsubstituted.

In some embodiments of this invention, when R$^2$ is 2-pyridyl and R$^3$ and R$^4$ are H, then Q-Q$^1$ is not

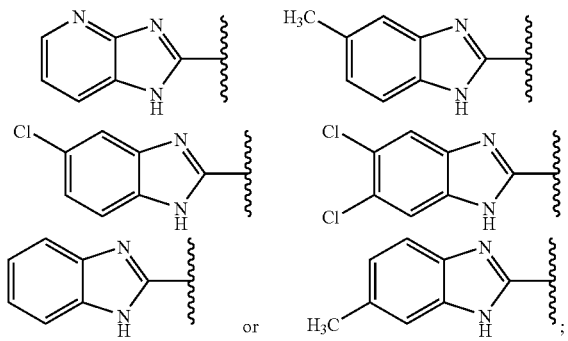

wherein Q-Q$^1$ is a bicyclic ring formed by the fusion of Q$^1$ to Q.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "fully unsaturated", when referring to a ring, means an aromatic ring.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "alkylidene chain" refers to a straight or branched carbon chain that may be fully saturated or have one or more units of unsaturation and has two points of attachment to the rest of the molecule.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —$CO_2$—, —OC(O)—, —C(O) CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound.

Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

Unless otherwise indicated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

The following abbreviations are used:

| | |
|---|---|
| DMF | dimethylformamide |
| DCM | dichloromethane |
| Ac | acetyl |
| THF | tetrahydrofuran |
| DMF | dimethylformamide |
| EtOAc | ethyl acetate |
| DMSO | dimethyl sulfoxide |
| Et$_2$O | diethylether |
| PE | petroleum ether |
| MeCN | acetonitrile |
| TCA | trichloroacetic acid |
| BuLi | butyllithium |
| ATP | adenosine triphosphate |
| NMP | N-methylpyrrolidone |
| m-CPBA | m-chloroperoxybenzoic Acid |
| EtOH | ethanol |
| MeOH | methanol |
| Ph | phenyl |
| Me | methyl |
| Et | ethyl |
| HEPES | 4-(2-hydroxyethyl)-1-piperazineethanesulfonic acid |
| BSA | bovine serum albumin |
| DTT | dithiothreitol |
| NMR | nuclear magnetic resonance |
| TLC | thin layer chromatography |
| HPLC | high performance liquid chromatography |
| LCMS | liquid chromatography-mass spectrometry |
| Rt | retention time |

In one embodiment of this invention, is

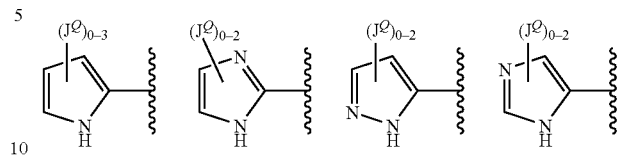

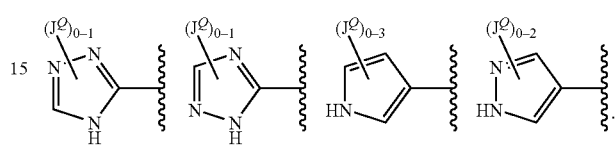

It should be understood that J$^Q$ is a substituent on any carbon atom of the 5-membered heteroaryl ring. J$^Q$ is not a substituent on the nitrogen atom. The nitrogen atoms in Q, if substituted, are only substituted with H, as shown above. In some embodiments, Q$^1$ is optionally substituted phenyl.

In certain embodiments, the fused bicyclic ring formed by Q and Q$^1$ is described as Q-Q$^1$. In some embodiments, Q-Q$^1$ is

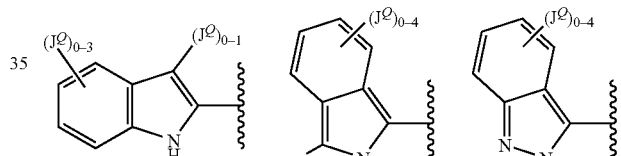

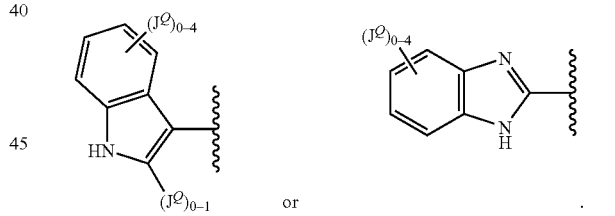

In some embodiments, Q-Q$^1$ is

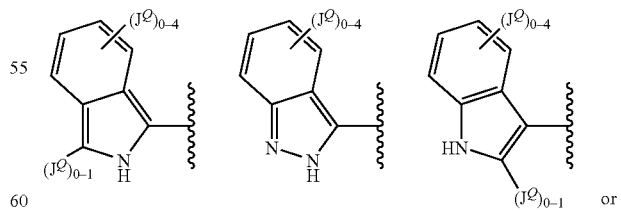

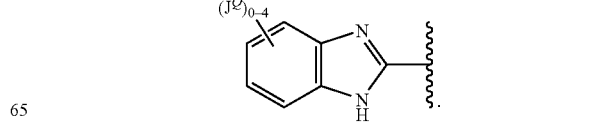

In some embodiments, Q-Q¹ is

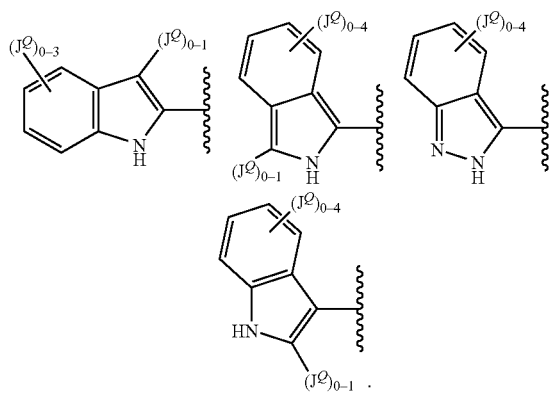

or

In some embodiments, Q-Q¹ is

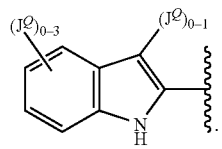

In some embodiments,
each $J^Q$ is independently selected from CN, halo, $C_{1-6}$alkyl, $C_{1-4}$haloalkyl, —OR$^o$, —N(R$^o$)$_2$, —SR$^o$, —($C_{1-6}$alkyl)-OR$^o$, —($C_{1-6}$alkyl)-N(R$^o$)$_2$, —($C_{1-6}$alkyl)-SR$^o$, —(U)$_m$—($C_{6-10}$aryl) —(U)$_m$—(5-12 membered heteroaryl), —(U)$_m$—(3-12 membered heterocyclyl), —(U)$_m$—($C_{3-10}$cycloaliphatic), —C(O)OR$^o$, —NR$^o$COR$^o$, —COR$^o$, —CON(R$^o$)$_2$, —SO$_2$R$^o$, and —SO$_2$N(R$^o$)$_2$;
U is a $C_{1-10}$alkyl, wherein 0-1 methylene units are independently replaced by, —NR$^o$—, —O—, or —S—;
m is 0 or 1.

In some embodiments, $J^Q$ is CN, halo, $C_{1-6}$alkyl, $C_{1-4}$haloalkyl, —OR$^o$, —N(R$^o$)$_2$, —SR$^o$, —NH—($C_{1-6}$alkyl)-(3-8 membered heterocyclyl), —O—($C_{1-6}$alkyl)-(3-8 membered heterocyclyl), 3-8 membered heterocyclyl, —C(O)OR$^o$, —NR$^o$COR$^o$, —COR$^o$, —CON(R$^o$)$_2$, —SO$_2$R$^o$, or —SO$_2$N(R$^o$)$_2$; In some embodiments, $J^Q$ is —N(R$^o$)$_2$, OR$^o$, or optionally substituted 5-8 membered heterocyclyl. In some embodiments, said 5-8 membered heterocyclyl contains 0-2 nitrogen atoms. In certain embodiments, $J^Q$ is an optionally substituted group selected from piperidinyl, piperazinyl, and pyrrolidinyl.

In some embodiments, each $J^Q$ is optionally and independently substituted with 0-5 $R^X$; in other embodiments, 0-3 $R^X$; in yet other embodiments, 0-1 $R^X$.

In other embodiments of this invention, $R^X$ is selected from H, methyl, ethyl, n-propyl, isopropyl, cyclopropyl, sec-butyl, n-butyl, t-butyl, halogen, NO$_2$, CN, NH$_2$, NH($C_{1-4}$aliphatic), N($C_{1-4}$aliphatic)$_2$, OH, O($C_{1-4}$aliphatic), CO$_2$H, OCF$_3$, CF$_3$, COCH$_3$, —($C_{1-4}$alkyl)$_{0-1}$-O($C_{1-4}$alkyl), —($C_{1-4}$alkyl)$_{0-1}$-O($C_{1-4}$alkyl)OH, —($C_{1-4}$alkyl)$_{0-1}$-NH($C_{1-4}$alkyl), —($C_{1-4}$alkyl)$_{0-1}$-N($C_{1-4}$alkyl)$_2$, —($C_{1-4}$alkyl)$_{0-1}$-NH$_2$, and —($C_{1-4}$alkyl)$_{0-1}$-(3-7 membered heterocyclyl).

In some embodiments, each $R^X$ is optionally and independently substituted with 0-5 J$^o$; in some embodiments, 0-3 J$^o$; in some embodiments, 0-1 J$^o$.

In yet other embodiments of this invention, $R^o$ is selected from H, methyl, ethyl, n-propyl, isopropyl, cyclopropyl, sec-butyl, n-butyl, t-butyl, COCH$_3$, —($C_{1-4}$alkyl)-O($C_{1-4}$alkyl), —($C_{1-4}$alkyl)-O($C_{1-4}$alkyl)OH, —($C_{1-4}$alkyl)-NH($C_{1-4}$alkyl), —($C_{1-4}$alkyl)-N($C_{1-4}$alkyl)$_2$, —($C_{1-4}$alkyl)-NH$_2$, and —($C_{1-4}$alkyl)$_{0-1}$-(3-7 membered heterocyclyl).

In some embodiments, each $R^o$ is optionally and independently substituted with 0-5 J$^o$; in some embodiments, 0-3 J$^o$; in some embodiments, 0-1 J$^o$;

In some embodiments, each $R^3$ and $R^4$ is independently H. In certain embodiments, $R^3$ and $R^4$ are both H.

In another embodiment of this invention, $R^2$ is a 5-8 membered monocyclyl. In some embodiments, $R^2$ is $C_{3-8}$cycloaliphatic. In other embodiments, $R^2$ is a 5-6 membered aryl or heteroaryl ring. In yet other embodiments, $R^2$ is an optionally substituted 6-membered aryl or 6-membered heteroaryl ring having 0-2 nitrogen atoms. In some embodiments, $R^2$ is a phenyl, pyridyl, pyrazinyl, or pyrimidyl ring. In certain embodiments, $R^2$ is a phenyl, 3-pyridyl, 4-pyridyl, pyrazinyl, 2,4-pyrimidyl, or 3,5-pyrimidyl ring.

In some embodiments, $R^2$ is optionally substituted phenyl. In other embodiments, $R^2$ is a phenyl, 3-pyridyl, pyrazinyl, 2,4-pyrimidyl, or 3,5-pyrimidyl ring.

In certain embodiments, $R^2$ is optionally substituted with 0-5 $J^{R2}$; in some embodiments, 0-3 $J^{R2}$; in some embodiments, 0-1 $J^{R2}$.

In some embodiments of this invention, $J^{R2}$ is selected from halo, $C_{1-6}$alkyl, $C_{6-10}$aryl, —$C_{1-6}$alkyl-$C_{6-10}$aryl, $C_{1-4}$haloalkyl, —OR$^o$, —N(R$^o$)$_2$, —SR$^o$, NO$_2$, CN, 3-10 membered heterocyclyl, —($C_{1-6}$alkyl)-OR$^o$, —($C_{1-6}$alkyl)-N(R$^o$)$_2$, —($C_{1-6}$alkyl)-SR$^o$, —C(O)OR$^o$, —NR$^o$COR$^o$, —COR$^o$, —CON(R$^o$)$_2$, —SO$_2$R$^o$, —SO$_2$N(R$^o$)$_2$, or $C_{1-6}$ alkylidene chain, wherein up to three methylene units of the chain are independently replaced by, —NR$^o$—, —O—, —S—, —SO—, SO$_2$—, or —CO— in a chemically stable arrangement. In some embodiments, $J^{R2}$ is selected from —OR$^o$, —N(R$^o$)$_2$, —SR$^o$, —($C_{1-6}$alkyl)-OR$^o$, —($C_{1-6}$alkyl)-N(R$^o$)$_2$, or —($C_{1-6}$alkyl)-SR$^o$.

In some embodiments, each $J^{R2}$ is independently and optionally substituted with 0-5 $R^X$; in some embodiments, 0-3 $R^X$; in some embodiments, 0-1 $R^X$.

In some embodiments, the variables are as depicted in the compound of Table 1.

Accordingly, a representative example of a compound of formula I is depicted in Table 1:

TABLE 1

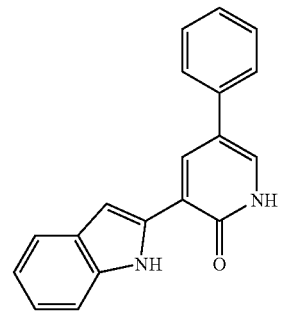

I.1

General Synthetic Methodology

The compounds of this invention may be prepared in general by methods such as those depicted in the general schemes below, and the preparative examples that follow.

Scheme 1

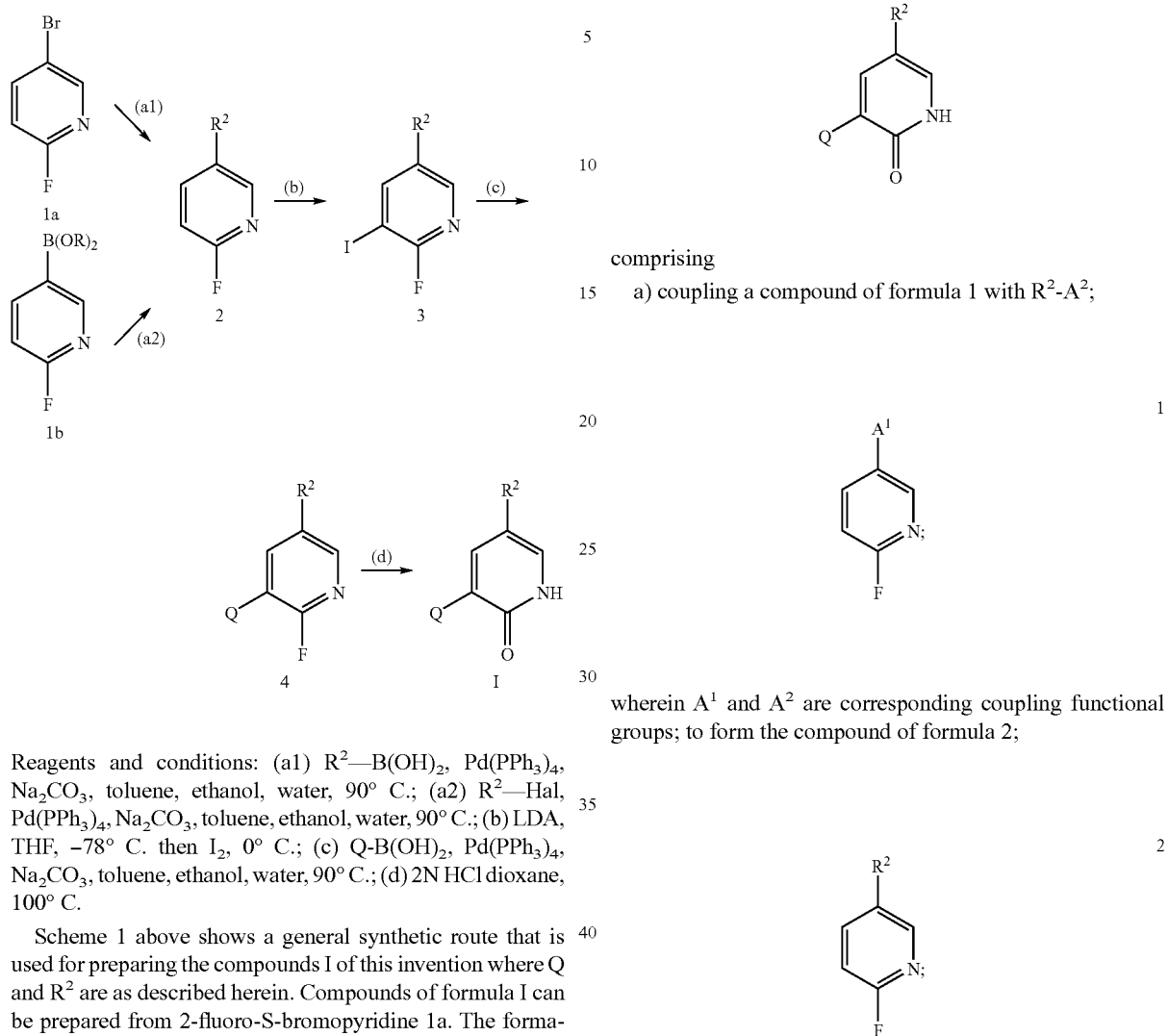

Reagents and conditions: (a1) R²—B(OH)₂, Pd(PPh₃)₄, Na₂CO₃, toluene, ethanol, water, 90° C.; (a2) R²—Hal, Pd(PPh₃)₄, Na₂CO₃, toluene, ethanol, water, 90° C.; (b) LDA, THF, −78° C. then I₂, 0° C.; (c) Q-B(OH)₂, Pd(PPh₃)₄, Na₂CO₃, toluene, ethanol, water, 90° C.; (d) 2N HCl dioxane, 100° C.

Scheme 1 above shows a general synthetic route that is used for preparing the compounds I of this invention where Q and R² are as described herein. Compounds of formula I can be prepared from 2-fluoro-5-bromopyridine 1a. The formation of derivatives 2 is achieved by treating 1a with a boronic acid in the presence of palladium as a catalyst by using the Suzuki coupling methods that are well known in the art. The reaction is amenable to a variety of boronic acids R²—B(OH)₂. Alternatively, compounds of formula I can be prepared from 2-fluoropyridine boronic acid or ester 1b. The formation of derivatives 2 is achieved by treating 1b with a halide in the presence of palladium as a catalyst by using methods similar to the one described in *Tetrahedron*, 2002, 58, 14, 2885-2890. The reaction is amenable to a variety of halides R²-Hal. Deprotonation of 2 with LDA, followed by addition of iodine, leads to the formation of 3 which can be reacted with a aryl boronic acid in the presence of palladium as a catalyst to give compounds 4, using Suzuki coupling methods that are well known in the art. The reaction is amenable to a variety of aryl boronic acids Q-B(OH)₂. Deprotection of 4 in acidic conditions leads to the formation of I.

Accordingly, this invention also provides a process for preparing a compound of this invention.

One embodiment of this invention provides a process for preparing a compound of formula I:

comprising
a) coupling a compound of formula 1 with R²-A²;

wherein A¹ and A² are corresponding coupling functional groups; to form the compound of formula 2;

wherein R² is as defined herein;
b) iodinating a compound of formula 2 under suitable conditions to form a compound of formula 3;

wherein R² is as defined herein;

c) reacting the compound of formula 3;

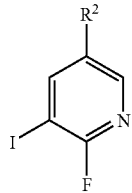
3 wherein $R^2$ is as defined herein;

with Q-B(OH)$_2$ under Pd coupling conditions to form a compound of formula 4;

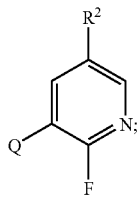
4 wherein $R^2$ is as defined herein;

d) heating the compound of formula 4 under acidic conditions to form the compound of formula I wherein Q and $R^2$ are as defined herein.

Coupling functional groups are defined as any two groups that, in the presence of a catalyst, are coupled together. Examples of coupling functional groups include, but are not limited to, —B(OH)$_2$ and a halogen (Suzuki coupling); —ZnBr and a halogen (Negishi coupling), and —SnBu$_3$ and a halogen (Stille coupling). Examples of catalysts include, but are not limited to, NiP(Ph$_3$)$_4$, Pd(II)acetate, Pd(dppf)Cl$_2$, tetrakis(triphenylphosphine) palladium, and bis(triphenylphosphine) palladium(II) chloride.

Another embodiment of this invention provides a process for preparing a compound of formula I:

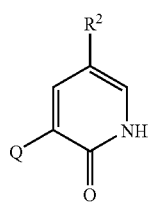
I comprising a) Reacting a compound of formula 3

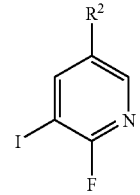
3 wherein $R^2$ is as defined herein;

with Q-B(OH)$_2$ under suitable coupling conditions to form a compound of formula 4;

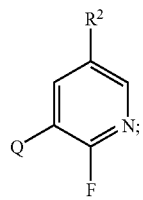
4 wherein $R^2$ is as defined herein;

b) heating the compound of formula 4 under acidic conditions to form the compound of formula I wherein Q and $R^2$ are as defined herein.

Suitable coupling conditions are known to those skilled in the art and include, but are not limited to, the use of a palladium catalyst (e.g. Pd(II)acetate, Pd(dppf)Cl$_2$, or PdP(Ph$_3$)$_4$), a suitable solvent (e.g. DCM or THF), and a suitable base (e.g. K$_2$CO$_3$ or Na$_2$CO$_3$).

Yet another embodiment of this invention provides a process comprising a) coupling a compound of formula 1 with $R^2$-$A^2$;

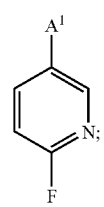
1 wherein $A^1$ and $A^2$ are corresponding coupling functional groups; to form a compound of formula 2;

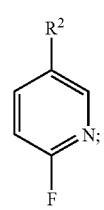
2 wherein $R^2$ is as defined herein;

b) iodinating the compound of formula 2 under suitable conditions to form a compound of formula 3;

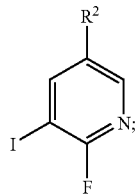

wherein R² is as defined herein.

Pharmaceutical Compositions

As discussed above, the present invention provides compounds that are inhibitors of protein kinases, and thus the present compounds are useful for the treatment of diseases, disorders, and conditions including, but not limited to an autoimmune, inflammatory, proliferative, or hyperproliferative disease or an immunologically-mediated disease. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative or salt thereof which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a Tec family (e.g., Tec, Btk, Itk/Emt/Tsk, Bmx, Txk/Rlk) protein kinases kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Methods of Treatment

As described generally above, the compounds of the invention are useful as inhibitors of protein kinases. In one embodiment, the compounds and compositions of the invention are inhibitors of one or more of Tec family (e.g., Tec, Btk, Itk/Emt/Tsk, Bmx, Txk/Rlk) kinase, and thus, without wishing to be bound by any particular theory, the compounds and compositions are particularly useful for treating or lessening the severity of a disease, condition, or disorder where activation of one or more of a Tec family (e.g., Tec, Btk, Itk/Emt/Tsk, Bmx, Txk/Rlk) kinase is implicated in the disease, condition, or disorder. When activation of Tec family (e.g., Tec, Btk, Itk/Emt/Tsk, Bmx, Txk/Rlk) is implicated in a particular disease, condition, or disorder, the disease, condition, or disorder may also be referred to as a "Tec family (e.g., Tec, Btk, Itk/Emt/Tsk, Bmx, Txk/Rlk)-mediated disease" or disease symptom.

Accordingly, in another aspect, the present invention provides a method for treating or lessening the severity of a disease, condition, or disorder where activation or one or more of Tec family (e.g., Tec, Btk, Itk/Emt/Tsk, Bmx, Txk/Rlk) is implicated in the disease state.

In yet another aspect, a method for the treatment or lessening the severity of a Tec family (e.g., Tec, Btk, Itk/Emt/Tsk, Bmx, Txk/Rlk)-mediated diseases is provided comprising administering an effective amount of a compound, or a pharmaceutically acceptable composition comprising a compound to a subject in need thereof. In some embodiments, said Tec-family-mediated disease is an Itk-mediated disease. In certain embodiments of the present invention an "effective amount" of the compound or pharmaceutically acceptable composition is that amount effective for a Tec family (e.g., Tec, Btk, Itk/Emt/Tsk, Bmx, Txk/Rlk)-mediated disease. The compounds and compositions, according to the method of the present invention, may be administered using any amount and any route of administration effective for treating or lessening the severity of a Tec family (e.g., Tec, Btk, Itk/Emt/Tsk, Bmx, Txk/Rlk)-mediated disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The term "Tec family tyrosine kinases-mediated condition", as used herein means any disease or other deleterious condition in which Tec family kinases are known to play a role. Such conditions include, without limitation, autoimmune, inflammatory, proliferative, and hyperproliferative diseases and immunologically mediated diseases including rejection of transplanted organs or tissues and Acquired Immunodeficiency Syndrome (AIDS).

For example, Tec family tyrosine kinases-mediated conditions include diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additionally, Tec family tyrosine kinases diseases include, without limitation, those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

Tec family tyrosine kinases-mediated conditions also include diseases of the bone and joints including, without limitation, (pannus formation in) rheumatoid arthritis, seronegative spondyloarthropathies (including ankylosing spondylitis, psoriatic arthritis and Reiter's disease), Behcet's disease, Sjogren's syndrome, and systemic sclerosis.

Tec family kinases-mediated conditions also include diseases and disorders of the skin, including, without limitation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata and vernal conjunctivitis.

Tec family tyrosine kinases-mediated conditions also include diseases and disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

Tec family tyrosine kinases-mediated conditions also include those diseases and disorders of other tissues and systemic disease, including, without limitation, multiple sclerosis, atherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

Tec family tyrosine kinases-mediated conditions also include allograft rejection including, without limitation, acute and chronic allograft rejection following for example transplantation of kidney, heart, liver, lung, bone marrow, skin and cornea; and chronic graft versus host disease.

Combination Therapies

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, for example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Medical Devices

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

In Vitro Uses

The activity of a compound utilized in this invention as an inhibitor of a Tec family (e.g., Tec, Btk, Itk/Emt/Tsk, Bmx, Txk/Rlk) kinase may be assayed in vitro, in vivo or in a cell line. In vitro assays include assays that determine inhibition of either the phosphorylation activity or ATPase activity of activated Tec family (e.g., Tec, Btk, Itk/Emt/Tsk, Bmx, Txk/Rlk) kinase. Alternate in vitro assays quantitate the ability of the inhibitor to bind to a Tec family (e.g., Tec, Btk, Itk/Emt/Tsk, Bmx, Txk/Rlk) kinase. Inhibitor binding may be measured by radiolabelling the inhibitor prior to binding, isolating the inhibitor/Tec family (e.g., Tec, Btk, Itk/Emt/Tsk, Bmx, Txk/Rlk), complex and determining the amount of radiolabel bound. Alternatively, inhibitor binding may be determined by running a competition experiment where new inhibitors are incubated with a Tec family (e.g., Tec, Btk, Itk/Emt/Tsk, Bmx, Txk/Rlk) kinase bound to known radioligands.

The term "measurably inhibit", as used herein means a measurable change in a Tec family (e.g., Tec, Btk, Itk/Emt/Tsk, Bmx, Txk/Rlk) kinase activity between a sample comprising said composition and a Tec family (e.g., Tec, Btk, Itk/Emt/Tsk, Bmx, Txk/Rlk) kinase and an equivalent sample comprising a Tec family (e.g., Tec, Btk, Itk/Emt/Tsk, Bmx, Txk/Rlk) kinase in the absence of said composition.

Another aspect of the invention provides a method for modulating enzyme activity by contacting a compound of formula I with a protein kinase. In some embodiments, said protein kinase is a Tec family (e.g., Tec, Btk, Itk/Emt/Tsk, Bmx, Txk/Rlk) kinase.

Biological Sample

Another aspect of the invention relates to inhibiting protein kinase activity in a biological sample or a patient, which method comprises administering to the patient, or contacting said biological sample with a compound of formula I or a composition comprising said compound. The term "biological sample", as used herein, means an in vitro or an ex vivo sample, and includes, without limitation, cell cultures or extracts thereof; biopsied material obtained from a mammal or extracts thereof; and blood, saliva, urine, feces, semen, tears, or other body fluids or extracts thereof. In some embodiments, said protein kinase is a Tec family (e.g., Tec, Btk, Itk/Emt/Tsk, Bmx, Txk/Rlk) kinase.

Inhibition of Tec family (e.g., Tec, Btk, Itk/Emt/Tsk, Bmx, Txk/Rlk) kinase activity in a biological sample is useful for a variety of purposes that are known to one of skill in the art. Examples of such purposes include, but are not limited to, blood transfusion, organ-transplantation, biological specimen storage, and biological assays.

The compounds of this invention may be prepared in general by methods known to those skilled in the art for analogous compounds or by those methods depicted in the Examples below.

EXAMPLES

Example 1

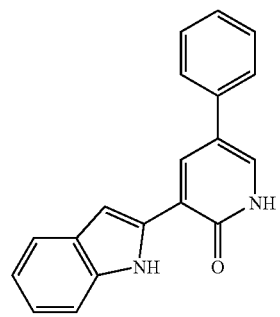

3-(1H-indol-2-yl)-5-phenylpyridin-2(1H)-one I-1

Method 1

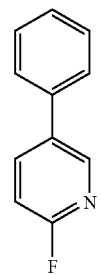

2-fluoro-5-phenylpyridine

To a solution of 5-bromo-2-fluoropyridine (2.33 g, 13.2 mmol) in toluene (100 mL) and ethanol (25 mL) were added Pd(PPh3)4 (764 mg, 0.66 mmol), phenylboronic acid (2.42 g, 19.8 mmol, 1.5 eq) and a solution of sodium carbonate (9.6 g, 90.7 mmol, 6.85 eq) in water (50 mL). The reaction mixture was heated to 90 C for 2 hours, allowed to cool to room temperature and partitioned between water and ethyl acetate. The organic layer was dried and evaporated and the residue purified by column chromatography (petrol/ethyl acetate gradient) to afford the title compound as a colorless oil (2.14 g, 93%)

Method 2

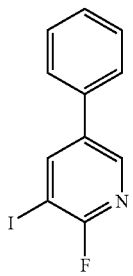

2-fluoro-3-iodo-5-phenylpyridine 2.5 M n-BuLi in hexanes (460 μL, 1.15 mmol, 1.0 Eq.) was added dropwise to a stirred solution of diisopropylamine (162 μL, 1.15 mmol, 1.0 Eq.) in anhydrous THF (20 mL) at −78° C. under nitrogen. The reaction was warmed to 0° C. and stirred for 30 minutes. The reaction was cooled to −78° C. and a solution of 2-fluoro-5-phenyl-pyridine (200 mg, 1.15 mmol, 1.0 Eq.) in anhydrous THF (5 mL) was added dropwise. The reaction was stirred at −78° C. for 2 hours then warmed to 0° C. and stirred for another 2 hours before warming to ambient temperature and stirring for a further 2 hours. Saturated aqueous sodium thiosulfate (20 mL) was added and the aqueous layer extracted with Et$_2$O (3×30 mL). The combined organic extracts were dried (MgSO$_4$), filtered and the solvent removed in vacuo. The residue was purified by column chromatography on SiO$_2$, eluting with 5% Et$_2$O/petroleum ether to give the desired compound as a white solid (114 mg, 0.38 mmol, 33%).

Method 3

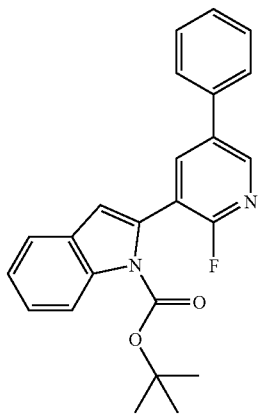

tert-butyl 2-(2-fluoro-5-phenylpyridin-3-yl)-1H-indole-1-carboxylate

Na$_2$CO$_3$ (279 mg, 2.63 mmol, 6.9 Eq.) in water (2 mL) was added to a mixture of 2-fluoro-3-iodo-5-phenyl-pyridine (114 mg, 0.38 mmol, 1.0 Eq.), Pd(PPh$_3$)$_4$ (44 mg, 0.04 mmol, 10 mol %) and 1-boc-indole-2-boronic acid (116 mg, 0.57 mmol, 1.5 Eq.) in toluene (5 mL) and EtOH (1 mL). The reaction was heated at reflux under nitrogen overnight. After cooling to ambient temperature the reaction mixture was diluted with water (10 mL) and extracted with EtOAc (3×20 mL). The combined organic extracts were dried (MgSO$_4$), filtered and the solvent removed in vacuo. The residue was purified by column chromatography on SiO$_2$, eluting with 10% Et$_2$O/petroleum ether to give the desired compound as a white foam (113 mg, 0.29 mmol, 76%).

Method 4

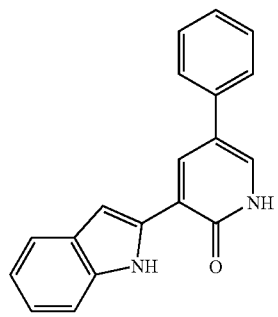

3-(1H-indol-2-yl)-5-phenylpyridin-2(1H)-one I-1

Concentrated HCl (0.5 mL) was added dropwise to a stirred solution of 2-(2-fluoro-5-phenyl-pyridin-3-yl)-indole-1-carboxylic acid tert-butyl ester (113 mg, 0.29 mmol, 1.0 eq.) in dioxane (6 mL) and water (2 mL). The reaction was heated at reflux overnight. The reaction was cooled to ambient temperature and the solvent removed in vacuo. The crude residue was partitioned between water (10 mL) and EtOAc (15 mL) and the aqueous layer extracted with EtOAc (3×15 mL). The combined organic extracts were dried (MgSO$_4$), filtered and the solvent removed in vacuo. The residue was purified by column chromatography on SiO$_2$, eluting with 50% EtOAc/petroleum ether to 100% EtOAc to 10% MeOH/DCM to give the desired product as a yellow solid (25 mg, 0.09 mmol, 30%).

The characterization data for compound I-1 is summarized in Table 2 below and includes HPLC, LC/MS (observed) and $^1$H NMR data.

$^1$H NMR data is summarized in Table 2 and was found to be consistent with structure. $^1$H-NMR spectra were recorded at 400 MHz using a Bruker DPX 400 instrument in deuterated DMSO, unless otherwise indicated.

LCMS samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions are 5%-100% acetonitrile-methanol over 4.5 mins gradient time and 6.2 mins run time on an ACE C8 3.0×75 mm column. Flow rate is 1.0 ml/min.

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm
Gradient: 0-100% acetonitrile+methanol 60:40 (20 mM Tris phosphate)
Flow rate: 1.5 mL/minute
Detection: 225 nm.
Compound numbers correspond to the compound numbers listed in Table 1.

TABLE 2

Characterization data for selected compound of formula I

| Compound No | M + 1(obs) | Rt (min) | $^1$H-NMR |
|---|---|---|---|
| I.1 | 287.5 | 9.7 | 6.99(1H, t), 7.10(1H, t), 7.35(1H, t), 7.41(1H, s), 7.47(3H, t), 7.54(1H, d), 7.73(2H, d), 7.75(1H, brd s), 8.46(1H, d), 11.54(1H, s), 12.28(1H, brd s) |

Example 2

Itk Inhibition Assay

The compounds of the present invention can be evaluated as inhibitors of human Itk kinase using either a radioactivity-based or spectrophotometric assay. In general, compounds of the invention, including the compound in Table 1, are effective for the inhibition of ITK. Specifically, compound I.1 has a Ki value of <2 uM.

Itk Inhibition Assay: Radioactivity-Based Assay

Assays are carried out in a mixture of 100 mM HEPES (pH 7.5), 10 mM MgCl$_2$, 25 mM NaCl, 0.01% BSA and 1 mM DTT. Final substrate concentrations are 15 µM [γ-$^{33}$P]ATP (400 µCi $^{33}$P ATP/µmol ATP, Amersham Pharmacia Biotech/Sigma Chemicals) and 2 µM peptide (SAM68 protein Δ332-443). Assays are carried out at 25° C. in the presence of 30 nM Itk. An assay stock buffer solution is prepared containing all of the reagents listed above, with the exception of ATP and the test compound of interest. 50 µL of the stock solution is placed in a 96 well plate followed by addition of 1.5 µL of DMSO stock containing serial dilutions of the test compound (typically starting from a final concentration of 15 µM with 2-fold serial dilutions) in duplicate (final DMSO concentration 1.5%). The plate is pre-incubated for 10 minutes at 25° C. and the reaction initiated by addition of 50 µL [γ-$^{33}$P]ATP (final concentration 15 µM).

The reaction is stopped after 10 minutes by the addition of 50 µL of a TCA/ATP mixture (20% TCA, 0.4 mM ATP). A Unifilter GF/C 96 well plate (Perkin Elmer Life Sciences, Cat no. 6005174) is pretreated with 50 µL Milli Q water prior to the addition of the entire reaction mixture (150 µL). The plate is washed with 200 µL Milli Q water followed by 200 µL of a TCA/ATP mixture (5% TCA, 1 mM ATP). This wash cycle is repeated a further 2 times. After drying, 30 µL Optiphase 'SuperMix' liquid scintillation cocktail (Perkin Elmer) is added to the well prior to scintillation counting (1450 Microbeta Liquid Scintillation Counter, Wallac).

IC50 data are calculated from non-linear regression analysis of the initial rate data using the Prism software package (GraphPad Prism version 3.0cx for Macintosh, GraphPad Software, San Diego Calif., USA). Assays are carried out in a mixture of 20 mM MOPS (pH 7.0), 10 mM MgCl$_2$, 0.1% BSA and 1 mM DTT. Final substrate concentrations in the assay are 7.5 µM [γ-$^{33}$P]ATP (400 µCi $^{33}$p ATP/µmol ATP, Amersham Pharmacia Biotech/Sigma Chemicals) and 3 µM peptide (SAM68 protein Δ332-443). Assays are carried out at 25° C. in the presence of 50 nM Itk. An assay stock buffer solution is prepared containing all of the reagents listed above, with the exception of ATP and the test compound of interest. 50 µL of the stock solution is placed in a 96 well plate followed by addition of 2 µL of DMSO stock containing serial dilutions of the test compound (typically starting from a final concentration of 50 µM with 2-fold serial dilutions) in duplicate (final DMSO concentration 2%). The plate is pre-incubated for 10 minutes at 25° C. and the reaction initiated by addition of 50 µL [γ-$^{33}$P]ATP (final concentration 7.5 µM).

The reaction is stopped after 10 minutes by the addition of 100 µL 0.2M phosphoric acid+0.01% TWEEN 20. A multi-screen phosphocellulose filter 96-well plate (Millipore, Cat no. MAPHN0B50) is pretreated with 100 µL 0.2M phosphoric acid+0.01% TWEEN 20 prior to the addition of 170 µL of the stopped assay mixture. The plate is washed with 4×200 µL 0.2M phosphoric acid+0.01% TWEEN 20. After drying, 30 µL Optiphase 'SuperMix' liquid scintillation cocktail (Perkin Elmer) is added to the well prior to scintillation counting (1450 Microbeta Liquid Scintillation Counter, Wallac).

Ki(app) data are calculated from non-linear regression analysis of the initial rate data using the Prism software package (GraphPad Prism version 3.0cx for Macintosh, GraphPad Software, San Diego Calif., USA).

Itk Inhibition Assay: Spectrophotometric Assay

Compound I.1 was screened for its ability to inhibit Itk using a standard coupled enzyme assay (Fox et al., Protein Sci., (1998) 7, 2249).

Assays were carried out in a mixture of 20 mM MOPS (pH 7.0), 10 mM MgCl$_2$, 0.1% BSA, 1 mM DTT, 2.5 mM phosphoenolpyruvate, 300 µM NADH, 30 µg/ml pyruvate kinase and 10 µg/ml lactate dehydrogenase. Final substrate concentrations in the assay were 100 µM ATP (Sigma Chemicals) and 3 µM peptide (Biotinylated SAM68 Δ332-443). Assays were carried out at 25° C. and in the presence of 100 nM Itk.

An assay stock buffer solution was prepared containing all of the reagents listed above, with the exception of ATP and the test compound of interest. 60 µl of the stock solution was placed in a 96 well plate followed by addition of 2 µl of DMSO stock containing serial dilutions of the test compound (typically starting from a final concentration of 15 µM). The plate was preincubated for 10 minutes at 25° C. and the reaction initiated by addition of 5 µl of ATP. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

Example 3

Btk Inhibition Assay

The compounds of the present invention can be evaluated as inhibitors of human Btk kinase using a radioactivity-based assay.

Btk Inhibition Assay: Radioactivity-Based Assay

Assays are carried out in a mixture of 20 mM MOPS (pH 7.0), 10 mM MgCl$_2$, 0.1% BSA and 1 mM DTT. Final substrate concentrations in the assay are 50 µM [γ-$^{33}$P]ATP (200 µCi $^{33}$P ATP/µmol ATP, Amersham Pharmacia Biotech, Amersham, UK/Sigma Chemicals) and 2 µM peptide (SAM68 Δ332-443). Assays are carried out at 25° C. and in the presence of 25 nM Btk. An assay stock buffer solution is prepared containing all of the reagents listed above, with the exception of the peptide and the test compound of interest. 75 μL of the stock solution is placed in a 96 well plate followed by addition of 2 μL of DMSO stock containing serial dilutions of the test compound (typically starting from a final concentration of 15 μM) in duplicate (final DMSO concentration 2%). The plate is preincubated for 15 minutes at 25° C. and the reaction initiated by addition of 25 μL peptide (final concentration 2 μM). Background counts are determined by the addition of 100 μL 0.2M phosphoric acid+0.01% TWEEN to control wells containing assay stock buffer and DMSO prior to initiation with peptide.

The reaction is stopped after 10 minutes by the addition of 100 μL 0.2M phosphoric acid+0.01% TWEEN. A multiscreen phosphocellulose filter 96-well plate (Millipore, Cat no. MAPHN0B50) is pretreated with 100 μL 0.2M phosphoric acid+0.01% TWEEN 20 prior to the addition of 170 μL of the stopped assay mixture. The plate is washed with 4×200 μL 0.2M phosphoric acid+0.01% TWEEN 20. After drying, 30 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis using the Prism software package (GraphPad Prism version 3.0cx for Macintosh, GraphPad Software, San Diego Calif., USA).

Example 4

Rlk Inhibition Assay

Compounds are screened for their ability to inhibit Rlk using a standard coupled enzyme assay (Fox et al., Protein Sci., (1998) 7, 2249). Assays are carried out in a mixture of 20 mM MOPS (pH 7.0), 10 mM MgCl2, 0.1% BSA and 1 mM DTT. Final substrate concentrations in the assay are 100 μM ATP (Sigma Chemicals) and 10 μM peptide (Poly Glu:Tyr 4:1). Assays are carried out at 30° C. and in the presence of 40 nM Rlk. Final concentrations of the components of the coupled enzyme system are 2.5 mM phosphoenolpyruvate, 300 μM NADH, 30 μg/ml pyruvate kinase and 10 μg/ml lactate dehydrogenase.

An assay stock buffer solution is prepared containing all of the reagents listed above, with the exception of ATP and the test compound of interest. 60 μl of the stock solution is placed in a 96 well plate followed by addition of 2 μl of DMSO stock containing serial dilutions of the test compound (typically starting from a final concentration of 7.5 μM). The plate is preincubated for 10 minutes at 30° C. and the reaction initiated by addition of 5 μl of ATP. Initial reaction rates are determined with a Molecular Devices SpectraMax Plus plate reader over a 10 minute time course. IC50 and Ki data are calculated from non-linear regression analysis using the Prism software package (GraphPad Prism version 3.0cx for Macintosh, GraphPad Software, San Diego Calif., USA).

In general, compounds of the invention are effective for the inhibition of RLK.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A compound of formula I:

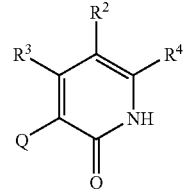

Formula I or a pharmaceutically accepted salt thereof, wherein $R^2$ is a 3-8-membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring having 0-5 heteroatoms independently selected from nitrogen, oxygen, or sulfur; wherein $R^2$ is optionally substituted with 0-5 $J^{R2}$;

each $R^3$ and $R^4$ is independently H, halogen, or $C_{1-4}$ aliphatic optionally substituted with 0-5 occurrences of halogen, OH, $OCH_3$, $OCF_3$, $NO_2$, $NH_2$, CN, $NHCH_3$, $SCH_3$, $N(CH_3)_2$, or $C_{1-2}$aliphatic optionally substituted 0-5 times with F;

Q is 5-membered heteroaryl containing 1-4 nitrogen atoms, wherein one of the nitrogen atoms is NH; each Q is optionally substituted with 0-3 $J^Q$ and is optionally fused to ring $Q^1$;

$Q^1$ is a 5-6 membered aryl or heteroaryl ring containing up to 3 heteroatoms selected from O, N, and S; each $Q^1$ is optionally substituted with 0-5 $J^Q$;

$J^{R2}$ and $J^Q$ are independently halogen, —$NO_2$, —CN, $C_{1-6}$ aliphatic, $C_{6-10}$aryl, —$C_{1-6}$alkyl-($C_{6-10}$aryl), 5-12 membered heteroaryl, —$C_{1-6}$alkyl-(5-12 membered heteroaryl), 3-12 membered heterocyclyl, —$C_{1-6}$alkyl-(3-12 membered heterocyclyl), $C_{3-10}$cycloaliphatic, —$C_{1-6}$alkyl-($C_{3-10}$cycloaliphatic), —OR°, —SR°, —N(R°)$_2$, —($C_{1-6}$alkyl)-OR°), —($C_{1-6}$alkyl)-N(R°)$_2$, —($C_{1-6}$alkyl)-SR°, —NR°C(O)R°, —NR°C(S)R°, —NR°C(O)N(R°)$_2$, —NR°C(S)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(S)R°, —C(O)N(R°)$_2$, —C(S)N(R°)$_2$, —OC(O)N(R°)$_2$, —OC(O)R°, —C(O)N(OR°)R°, —C(NOR°)R°, —S(O)$_2$R°, —S(O)$_3$R°, —SO$_2$N(R°)$_2$, —S(O)R°, —NR°SO$_2$N(R°)$_2$, —NR°SO$_2$R°, —N(OR°)R°, —C(=NH)—N(R°)$_2$, —P(O)$_2$R°, —PO(R°)$_2$—OPO(R°)$_2$, =O, =S, NNHR°, NN(R°)$_2$, =NNHC(O)R°, =NNHCO$_2$($C_{1-6}$alkyl), NNHSO$_2$($C_{1-6}$alkyl), =NOH, =NR°; or $C_{1-10}$ alkylidene chain, wherein up to three methylene units of the chain are independently replaced by —NR°—, —O—, —S—, —SO—, SO$_2$—, or —CO—; wherein each $J^{R2}$ and $J^Q$ is independently and optionally substituted with 0-5 $R^X$;

each $R^X$ is independently H, halogen, $NO_2$, CN, $NH_2$, NH($C_{1-4}$aliphatic), N($C_{1-4}$aliphatic)$_2$, OH, O($C_{1-4}$aliphatic), O($C_{1-4}$haloaliphatic), CO($C_{1-4}$aliphatic), $CO_2$H, $CO_2$($C_{1-4}$aliphatic), $C_{1-6}$aliphatic, $C_{1-4}$haloaliphatic, phenyl, —O(Ph), 5-6 membered heteroaryl, $C_{3-8}$cycloaliphatic, 5-8 membered heterocyclyl, —$C_{1-6}$aliphatic-(Ph), —$C_{1-6}$alkyl-(5-6 membered heteroaryl), —$C_{1-6}$alkyl-($C_{3-8}$cycloaliphatic), —$C_{1-6}$alkyl- (5-8 membered heterocyclyl), or $C_{1-10}$alkylidene chain wherein up to 2 methylene units of the chain are optionally replaced by O, N, or S; wherein each $R^X$ and is independently and optionally substituted with 0-5 $J^o$;

each $R^o$ is independently H, $C_{1-6}$aliphatic, $C_{1-4}$haloaliphatic, $CO(C_{1-4}$aliphatic), $CO_2(C_{1-4}$aliphatic), $—SO_2(C_{1-4}$aliphatic), $—SO_2$(phenyl), phenyl, 5-6 membered heteroaryl, 5-8 membered heterocyclyl, $C_{3-8}$cycloaliphatic, $—C_{1-6}$aliphatic-(Ph), $—C_{1-6}$alkyl-(5-6 membered heteroaryl), $—C_{1-6}$alkyl-(5-8 membered heterocyclyl), $—C_{1-6}$alkyl-($C_{3-8}$cycloaliphatic); or $C_{1-10}$alkylidene chain wherein up to 2 methylene units of the chain are optionally replaced by O, N, or S; wherein said $R^o$ is optionally substituted with 0-6 $J^o$;

or two $R^o$, on the same substituent or different substituents, taken together with the atom(s) to which each $R^o$ group is bound, form a 3-8 membered saturated, partially unsaturated, or fully unsaturated monocyclic or bicyclic ring having 0-4 heteroatoms independently selected from nitrogen, oxygen, or sulfur; wherein said ring is optionally and independently substituted with 0-4 occurrences of halogen, $NO_2$, CN, $C_{1-4}$aliphatic, $NH_2$, $NH(C_{1-4}$aliphatic), $N(C_{1-4}$aliphatic$)_2$, OH, $O(C_{1-4}$aliphatic), $CO_2H$, $CO_2(C_{1-4}$aliphatic), $O($halo$C_{1-4}$aliphatic), or halo$C_{1-4}$aliphatic, wherein each of the $R^oC_{1-4}$ aliphatic groups is unsubstituted;

each $J^o$ is independently halogen, $NO_2$, CN, $C_{1-4}$aliphatic, $—NH_2$, $—NH(C_{1-4}$aliphatic), $—N(C_{1-4}$ aliphatic$)_2$, $—OH$, $—O(C_{1-4}$aliphatic), $—CO_2H$, $—CO_2(C_{1-4}$aliphatic), $—O($halo$C_{1-4}$aliphatic), and halo$(C_{1-4}$aliphatic), wherein each of the $J^o$ $C_{1-4}$aliphatic groups is unsubstituted.

2. The compound according to claim 1, wherein when $R^2$ is 2-pyridyl and $R^3$ and $R^4$ are H; Q-$Q^1$ is not

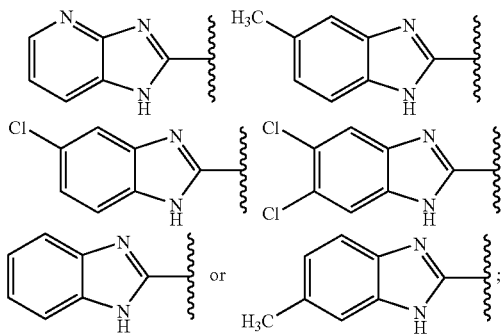

wherein Q-$Q^1$ is a bicyclic ring formed by the fusion of $Q^1$ to Q.

3. The compound according to claim 1 or claim 2, wherein Q is

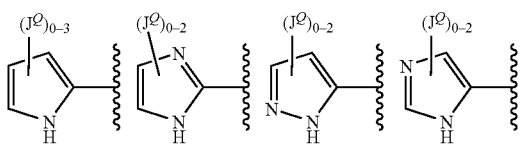

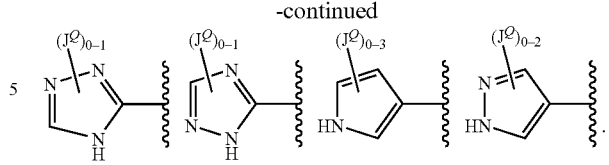

4. The compound according to claim 1 or claim 2, wherein $Q^1$ is phenyl optionally substituted with 0-5 $J^Q$.

5. The compound according to claim 4, wherein Q-$Q^1$ is

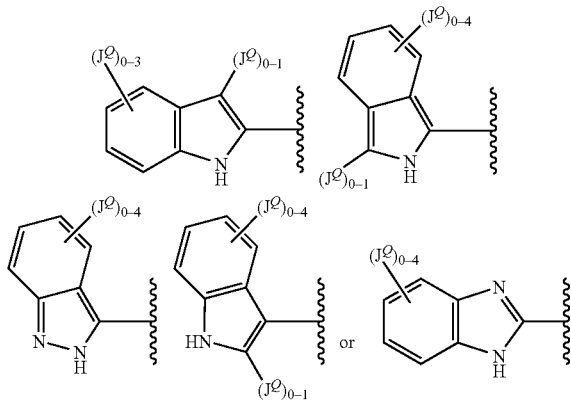

6. The compound according to claim 5, wherein Q-$Q^1$ is substituted with up to 3 $J^Q$ groups wherein each $J^Q$ is independently selected from CN, halo, $C_{1-6}$alkyl, $C_{1-4}$haloalkyl, $—OR^o$, $—N(R^o)_2$, $—SR^o$, $—(C_{1-6}$alkyl)-$OR^o$, $—(C_{1-6}$alkyl)-$N(R^o)_2$, $—(C_{1-6}$alkyl)-$SR^o$, $C_{6-10}$aryl, $—C_{1-6}$alkyl-($C_{6-10}$aryl), 5-12 membered heteroaryl, $—C_{1-6}$alkyl-(5-12 membered heteroaryl), 3-12 membered heterocyclyl, $—C_{1-6}$alkyl-(3-12 membered heterocyclyl), $C_{3-10}$cycloaliphatic, $—C_{1-6}$alkyl-($C_{3-10}$cycloaliphatic), $—C(O)OR^o$, $—NR^oCOR^o$, $—COP)$, $—CON(R^o)_2$, $—SO_2R^o$.

7. The compound according to claim 6, wherein each $J^Q$ is CN, halo, $C_{1-6}$alkyl, $C_{1-4}$haloalkyl, $—OR^o$, $—N(R^o)_2$, $—SPY$, 3-8 membered heterocyclyl, $—C(O)OR^o$, $—NR^o$-$COR^o$, $—COR^o$, $—CON(R^o)_2$, $—SO_2R^o$, or $—SO_2N(R^o)_2$; wherein each $J^Q$ is optionally and independently substituted with 0-5 $R^X$.

8. The compound according to claim 7, wherein $J^Q$ is $—N(R^o)_2$, $OR^o$, or a 5-8 membered heterocyclyl optionally substituted with 0-5 $R^X$.

9. The compound according to claim 8, wherein $J^Q$ is a group selected from piperidinyl, piperazinyl, and pyrrolidinyl wherein said group is optionally substituted with 0-5 $R^X$.

10. The compound according to claim 1 or claim 2, wherein $R^X$ is selected from H, methyl, ethyl, n-propyl, isopropyl, cyclopropyl, sec-butyl, n-butyl, t-butyl, halogen, $NO_2$, CN, $NH_2$, $NH(C_{1-4}$aliphatic), $N(C_{1-4}$aliphatic$)_2$, OH, $O(C_{1-4}$aliphatic), $CO_2H$, $OCF_3$, $CF_3$, $COCH_3$, $—(C_{1-4}$alkyl$)_{0-1}$-$O(C_{1-4}$alkyl), $—(C_{1-4}$alkyl$)_{0-1}$-$O(C_{1-4}$alkyl)OH, $—(C_{1-4}$alkyl$)_{0-1}$-$NH(C_{1-4}$alkyl), $—(C_{1-4}$alkyl$)_{0-1}$-$N(C_{1-4}$alkyl$)_2$, $—(C_{1-4}$alkyl$)_{0-1}$-$NH_2$, and $—(C_{1-4}$alkyl$)_{0-1}$-(3-7 membered heterocyclyl).

11. The compound according to claim 1 or claim 2, wherein $R^o$ is selected from H, methyl, ethyl, n-propyl, isopropyl, cyclopropyl, sec-butyl, n-butyl, t-butyl, $COCH_3$, $—(C_{1-4}$alkyl)-$O(C_{1-4}$alkyl), $—(C_{1-4}$alkyl)-$O(C_{1-4}$alkyl)OH, —(C$_{1-4}$alkyl)-NH(C$_{1-4}$alkyl), —(C$_{1-4}$alkyl)-N(C$_{1-4}$alkyl)$_2$, —(C$_{1-4}$alkyl)-NH$_2$, and —(C$_{1-4}$alkyl)$_{0-1}$-(3-7 membered heterocyclyl).

12. The compound according to claim 1 or claim 2, wherein each R$^3$ and R$^4$ is independently H.

13. The compound according to claim 12, wherein R$^3$ and R$^4$ are both H.

14. The compound according to claim 1 or claim 2, wherein R$^2$ is 5-8 membered monocyclyl optionally substituted with up to five J$^{R2}$.

15. The compound according to claim 14, wherein R$^2$ is C$_{3-8}$cycloaliphatic optionally substituted with up to five J$^{R2}$.

16. The compound according to claim 14, wherein R$^2$ is a 5-6 membered aryl or heteroaryl ring, wherein said ring is optionally substituted with up to five J$^{R2}$.

17. The compound according to claim 16, wherein R$^2$ is an optionally substituted 6-membered aryl or 6-membered heteroaryl ring having 0-2 nitrogen atoms, wherein said ring is optionally substituted with up to five J$^{R2}$.

18. The compound according to claim 17, wherein R$^2$ is a phenyl, pyridyl, pyrazinyl, or pyrimidyl ring, wherein said ring is optionally substituted with up to five J$^{R2}$.

19. The compound according to claim 18, wherein R$^2$ is a phenyl, 3-pyridyl, 4-pyridyl, pyrazinyl, 2,4-pyrimidyl, or 3,5-pyrimidyl ring, wherein said ring is optionally substituted with up to five J$^{R2}$.

20. The compound according to claim 14, wherein each J$^{R2}$ is selected from halo, C$_{1-6}$alkyl, C$_{6-10}$aryl, —C$_{1-6}$alkyl-C$_{6-10}$aryl, C$_{1-4}$haloalkyl, —OR$^o$, —N(R$^o$)$_2$, —SR$^o$, NO$_2$, CN, 3-10 membered heterocyclyl, —(C$_{1-6}$alkyl)-OR$^o$, —(C$_{1-6}$alkyl)-N(R$^o$)$_2$, —(C$_{1-6}$alkyl)-SR$^o$, —C(O)OR$^o$, —NR$^o$COR$^o$, —COR$^o$, —CON(R$^o$)$_2$, —SO$_2$R$^o$, —SO$_2$N(R$^o$)$_2$, or C$_{1-6}$ alkylidene chain, wherein up to three methylene units of the chain are independently replaced by, —NR$^o$—, —O—, —S—, —SO—, SO$_2$—, or —CO— in a chemically stable arrangement; each J$^{R2}$ is independently and optionally substituted with 0-5 R$^X$.

21. The compound according to claim 20, wherein each J$^{R2}$ is selected from —OR$^o$, —N(R$^o$)$_2$, —SR$^o$, —(C$_{1-6}$alkyl)-OR$^o$), —(C$_{1-6}$alkyl)-N(R$^o$)$_2$, or —(C$_{1-6}$alkyl)-SR$^o$; wherein each J$^{R2}$ is independently and optionally substituted with 0-5 R$^X$.

22. The compound according to claim 1 selected from the following:

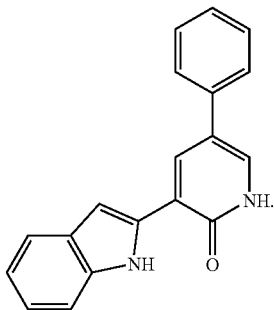

23. A composition comprising a compound of claim 1, and a pharmaceutically acceptable carrier, adjuvant, or vehicle.

24. A process for preparing a compound of formula I:

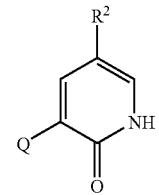

comprising
a) reacting a compound of formula 3

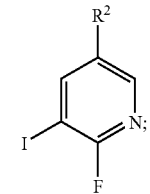

wherein R$^2$ is a 3-8-membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring having 0-5 heteroatoms independently selected from nitrogen, oxygen, or sulfur; wherein R$^2$ is optionally substituted with 0-5 J$^{R2}$;

J$^{R2}$ and J$^Q$ are each independently halogen, —NO$_2$, —CN, C$_{1-6}$aliphatic, C$_{6-10}$aryl, —C$_{1-6}$alkyl-(C$_{6-10}$aryl), 5-12 membered heteroaryl, —C$_{1-6}$alkyl-(5-12 membered heteroaryl), 3-12 membered heterocyclyl, —C$_{1-6}$alkyl-(3-12 membered heterocyclyl), C$_{3-10}$cycloaliphatic, —C$_{1-6}$alkyl-(C$_{3-10}$cycloaliphatic), —OR$^o$, —SR$^o$, —N(R$^o$)$_2$, —(C$_{1-6}$alkyl)-OR$^o$), —(C$_{1-6}$alkyl)-N(R$^o$)$_2$, —(C$_{1-6}$alkyl)-SR$^o$, —NR$^o$C(O)R$^o$, —NR$^o$C(S)R$^o$, —NR$^o$C(O)N(R$^o$)$_2$, —NR$^o$C(S)N(R$^o$)$_2$, —NR$^o$CO$_2$R$^o$, —NR$^o$NR$^o$C(O)R$^o$, —NR$^o$NR$^o$C(O)N(R$^o$)$_2$, —NR$^o$NR$^o$CO$_2$R$^o$, —C(O)C(O)R$^o$, —C(O)CH$_2$C(O)R$^o$, —CO$_2$R$^o$, —C(O)R$^o$, —C(S)R$^o$, —C(O)N(R$^o$)$_2$, —C(S)N(R$^o$)$_2$, —OC(O)N(R$^o$)$_2$, —OC(O)R$^o$, —C(O)N(OR$^o$)R$^o$, —C(NOR$^o$)R$^o$, —S(O)$_2$R$^o$, —S(O)$_3$R$^o$, —SO$_2$N(R$^o$)$_2$, —S(O)R$^o$, —NR$^o$SO$_2$N(R$^o$)$_2$, —NR$^o$SO$_2$R$^o$, —N(OR$^o$)R$^o$, —C(=NH)—N(R$^o$)$_2$, —P(O)$_2$R$^o$, —PO(R$^o$)$_2$, —OPO(R$^o$)$_2$, =O, =S, =NNHR$^o$, =NN(R$^o$)$_2$, =NNHC(O)R$^o$, =NNHCO$_2$(C$_{1-6}$alkyl), =NNHSO$_2$(C$_{1-6}$alkyl), =NOH, =NR$^o$; or C$_{1-10}$alkylidene chain, wherein up to three methylene units of the chain are independently replaced by —NR$^o$—, —O—, —S—, —SO—, SO$_2$—, or —CO—; wherein each J$^{R2}$ and J$^Q$ is independently and optionally substituted with 0-5 R$^X$;

each R$^X$ is independently H, halogen, NO$_2$, CN, NH$_2$, NH(C$_{1-4}$aliphatic), N(C$_{1-4}$aliphatic)$_2$, OH, O(C$_{1-6}$aliphatic), O(C$_{1-4}$haloaliphatic), CO(C$_{1-4}$aliphatic), CO$_2$H, CO$_2$(C$_{1-4}$aliphatic), C$_{1-6}$aliphatic, C$_{1-4}$haloaliphatic, phenyl, —O(Ph), 5-6 membered heteroaryl, C$_{3-8}$cycloaliphatic, 5-8 membered heterocyclyl, —C$_{1-6}$aliphatic-(Ph), —C$_{1-6}$alkyl-(5-6 membered heteroaryl), —C$_{1-6}$alkyl-(C$_{3-8}$cycloaliphatic), —C$_{1-6}$alkyl-(5-8 membered heterocyclyl), or C$_{1-10}$alkylidene chain wherein up to 2 methylene units of the chain are optionally replaced by O, N, or S; wherein each $R^X$ and is independently and optionally substituted with 0-5 $J^o$;

each $R^o$ is independently H, $C_{1-6}$aliphatic, $C_{1-4}$haloaliphatic, $CO(C_{1-4}$aliphatic), $CO_2(C_{1-4}$aliphatic), $-SO_2(C_{1-4}$aliphatic), $-SO_2$(phenyl), phenyl, 5-6 membered heteroaryl, 5-8 membered heterocyclyl, $C_{3-8}$cycloaliphatic, $-C_{1-6}$aliphatic-(Ph), $-C_{1-6}$alkyl-(5-6 membered heteroaryl), $-C_{1-6}$alkyl-(5-8 membered heterocyclyl), $-C_{1-6}$alkyl-($C_{3-8}$cycloaliphatic); or $C_{1-10}$alkylidene chain wherein up to 2 methylene units of the chain are optionally replaced by O, N, or S; wherein said $R^o$ is optionally substituted with 0-6 $J^o$;

or two $R^o$, on the same substituent or different substituents, taken together with the atom(s) to which each $R^o$ group is bound, form a 3-8 membered saturated, partially unsaturated, or fully unsaturated monocyclic or bicyclic ring having 0-4 heteroatoms independently selected from nitrogen, oxygen, or sulfur; wherein said ring is optionally and independently substituted with 0-4 occurrences of halogen, $NO_2$, CN, $C_{1-4}$aliphatic, $NH_2$, $NH(C_{1-4}$aliphatic), $N(C_{1-4}$aliphatic)$_2$, OH, $O(C_{1-4}$aliphatic), $CO_2H$, $CO_2(C_{1-4}$aliphatic), $O(haloC_{1-4}$aliphatic), or $haloC_{1-4}$aliphatic, wherein each of the $R^oC_{1-4}$ aliphatic groups is unsubstituted;

each $J^o$ is independently halogen, $NO_2$, CN, $NH_2$, $NH(C_{1-4}$aliphatic), $N(C_{1-4}$aliphatic)$_2$, OH, $O(C_{1-4}$aliphatic), $CO_2H$, $CO_2(C_{1-4}$aliphatic), $O(haloC_{1-4}$aliphatic), and $halo(C_{1-4}$haloaliphatic), wherein each $J^o$ $C_{1-4}$aliphatic groups is unsubstituted;

with Q-B(OH)$_2$ under suitable coupling conditions to form a compound of formula 4;

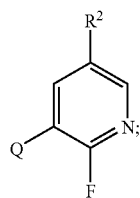

4 wherein $R^2$ is as defined above;

b) heating the compound of formula 4 under acidic conditions to form the compound of formula I wherein Q is a 5-membered heteroaryl containing 1-4 nitrogen atoms, wherein one of the nitrogen atoms is NH; each Q is optionally substituted with 0-3 $J^Q$ and is optionally fused to ring $Q^1$;

$Q^1$ is a 5-6 membered aryl or heteroaryl ring containing up to 3 heteroatoms selected from O, N, and S; each $Q^1$ is optionally substituted with 0-5 $J^o$, and $R^2$ is defined above.

25. The process of claim 24, wherein the compound of formula 3 is prepared, comprising b) coupling a compound of formula 1 with $R^2$-A2;

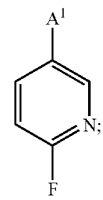

1 wherein A1 and A2 are corresponding coupling functional groups; to form a compound of formula 2;

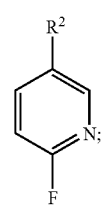

2 wherein $R^2$ is a 3-8-membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring having 0-5 heteroatoms independently selected from nitrogen, oxygen, or sulfur; wherein $R^2$ is optionally substituted with 0-5 $J^{R2}$;

$J^{R2}$ and $J^Q$ are each independently halogen, $-NO_2$, $-CN$, $C_{1-6}$aliphatic, $C_{6-10}$aryl, $-C_{1-6}$alkyl-($C_{6-10}$aryl), 5-12 membered heteroaryl, $-C_{1-6}$alkyl-(5-12 membered heteroaryl), 3-12 membered heterocyclyl, $-C_{1-6}$alkyl-(3-12 membered heterocyclyl), $C_{3-10}$cycloaliphatic, $-C_{1-6}$alkyl-($C_{3-10}$cycloaliphatic), $-OR^o$, $-SR^o$, $-N(R^o)_2$, $-(C_{1-6}$alkyl)-$OR^o$, $-(C_{1-6}$alkyl)-$N(R^o)_2$, $-(C_{1-6}$alkyl)-$SR^o$, $-NR^oC(O)R^o$, $-NR^oC(S)R^o$, $-NR^oC(O)N(R^o)_2$, $-NR^oC(S)N(R^o)_2$, $-NR^oCO_2R^o$, $-NR^oNR^oC(O)R^o$, $-NR^oNR^oC(O)N(R^o)_2$, $-NR^oNR^oCO_2R^o$, $-C(O)C(O)R^o$, $-C(O)CH_2C(O)R^o$, $-CO_2R^o$, $-C(O)R^o$, $-C(S)R^o$, $-C(O)N(R^o)_2$, $-C(S)N(R^o)_2$, $-OC(O)N(R^o)_2$, $-OC(O)R^o$, $-C(O)N(OR^o)R^o$, $-C(NOR^o)R^o$, $-S(O)_2R^o$, $-S(O)_3R^o$, $-SO_2N(R^o)_2$, $-S(O)R^o$, $-NR^oSO_2N(R^o)_2$, $-NR^oSO_2R^o$, $-N(OR^o)R^o$, $-C(=NH)-N(R^o)_2$, $-P(O)_2R^o$, $-PO(R^o)_2$, $-OPO(R^o)_2$, $=O$, $=S$, $=NNHR^o$, $=NN(R^o)_2$, $=NNHC(O)R^o$, $=NNHCO_2(C_{1-6}$alkyl), $=NNHSO_2(C_{1-6}$alkyl), $=NOH$, $=NR^o$; or $C_{1-10}$alkylidene chain, wherein up to three methylene units of the chain are independently replaced by $-NR^o-$, $-O-$, $-S-$, $-SO-$, $SO_2-$, or $-CO-$; wherein each $J^{R2}$ and $J^Q$ is independently and optionally substituted with 0-5 $R^X$;

each $R^X$ is independently H, halogen, $NO_2$, CN, $NH_2$, $NH(C_{1-4}$aliphatic), $N(C_{1-4}$aliphatic)$_2$, OH, $O(C_{1-4}$aliphatic), $O(C_{1-4}$haloaliphatic), $CO(C_{1-4}$aliphatic), $CO_2H$, $CO_2(C_{1-4}$aliphatic), $C_{1-6}$aliphatic, $C_{1-4}$haloaliphatic, phenyl, $-O(Ph)$, 5-6 membered heteroaryl, $C_{3-8}$cycloaliphatic, 5-8 membered heterocyclyl, $-C_{1-6}$aliphatic-(Ph), $-C_{1-6}$alkyl-(5-6 membered heteroaryl), $-C_{1-6}$alkyl-($C_{3-8}$cycloaliphatic), $-C_{1-6}$alkyl-(5-8 membered heterocyclyl), or $C_{1-10}$alkylidene chain wherein up to 2 methylene units of the chain are optionally replaced by O, N, or S; wherein each $R^X$ and is independently and optionally substituted with 0-5 $J^o$;

each $R^o$ is independently H, $C_{1-6}$aliphatic, $C_{1-4}$haloaliphatic, $CO(C_{1-4}$aliphatic), $CO_2(C_{1-4}$aliphatic), —$SO_2(C_{1-4}$aliphatic), —$SO_2$(phenyl), phenyl, 5-6 membered heteroaryl, 5-8 membered heterocyclyl, $C_{3-8}$cycloaliphatic, —$C_{1-6}$aliphatic-(Ph), —$C_{1-6}$alkyl-(5-6 membered heteroaryl), —$C_{1-6}$alkyl-(5-8 membered heterocyclyl), —$C_{1-6}$alkyl-($C_{3-8}$cycloaliphatic); or $C_{1-10}$alkylidene chain wherein up to 2 methylene units of the chain are optionally replaced by O, N, or S; wherein said $R^o$ is optionally substituted with 0-6 or two $R^o$, on the same substituent or different substituents, taken together with the atom(s) to which each $R^o$ group is bound, form a 3-8 membered saturated, partially unsaturated, or fully unsaturated monocyclic or bicyclic ring having 0-4 heteroatoms independently selected from nitrogen, oxygen, or sulfur; wherein said ring is optionally and independently substituted with 0-4 occurrences of halogen, $NO_2$, CN, $C_{1-4}$aliphatic, $NH_2$, $NH(C_{1-4}$aliphatic), $N(C_{1-4}$aliphatic)$_2$, OH, $O(C_{1-4}$aliphatic), $CO_2H$, $CO_2(C_{1-4}$aliphatic), O(halo$C_{1-4}$aliphatic), or halo$C_{1-4}$aliphatic, wherein each of the $R^o C_{1-4}$ aliphatic groups is unsubstituted;

each $J^o$ is independently halogen, $NO_2$, CN, $NH_2$, $NH(C_{1-4}$aliphatic), $N(C_{1-4}$aliphatic)$_2$, OH, $O(C_{1-4}$aliphatic), $CO_2H$, $CO_2(C_{1-4}$aliphatic), O(halo$C_{1-4}$aliphatic, and halo($C_{1-4}$haloaliphatic), wherein each $J^o$ $C_{1-4}$aliphatic groups is unsubstituted;

c) iodinating the compound of formula 2 under suitable conditions to form a compound of formula 3;

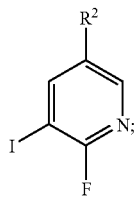

wherein $R^2$ is as defined above.

26. A compound of formula I'

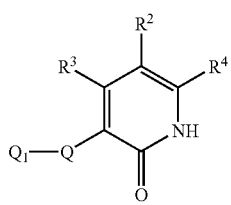

Formula I' or a pharmaceutically accepted salt thereof, wherein $R^2$ is a 3-8-membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring having 0-5 heteroatoms independently selected from nitrogen, oxygen, or sulfur; wherein $R^2$ is optionally substituted with 0-5 $J^{R2}$;

$J^{R2}$ is halogen, —$NO_2$, —CN, $C_{1-6}$ aliphatic, —$C_{6-10}$aryl, 5-12 heteroaryl, —$C_{1-6}$alkyl-(5-12 membered heteroaryl), 3-12 membered heterocyclyl, —$C_{1-6}$alkyl-(3-12 membered heterocyclyl), $C_{3-10}$cycloaliphatic, —$C_{1-6}$alkyl-($C_{3-10}$cycloaliphatic), —$OR^o$, —$SR^o$, —$N(R^o)_2$, —($C_{1-6}$alkyl)-$OR^o$), —($C_{1-6}$alkyl)-$N(R^o)_2$, —($C_{1-6}$alkyl)-$SR^o$, —$NR^oC(O)R^o$, —$NR^oC(S)R^o$, —$NR^oC(O)N(R^o)_2$, —$NR^oC(S)N(R^o)_2$, —$NR^oCO_2R^o$, —$NR^oNR^oC(O)R^o$, —$NR^oNR^oC(O)N(R^o)_2$, —$NR^oNR^oCO_2R^o$, —$C(O)C(O)R^o$, —$C(O)CH_2C(O)R^o$, —$CO_2R^o$, —$C(O)R^o$, —$C(S)R^o$, —$C(O)N(R^o)_2$, —$C(S)N(R^o)_2$, —$OC(O)N(R^o)_2$, —$OC(O)R^o$, —$C(O)N(OR^o)R^o$, —$C(NOR^o)R^o$, —$S(O)_2R^o$, —$S(O)_3R^o$, —$SO_2N(R^o)_2$, —$S(O)R^o$, —$NR^oSO_2N(R^o)_2$, —$NR^oSO_2R^o$, —$N(OR^o)R^o$, —$C(=NH)$—$N(R^o)_2$, —$P(O)_2R^o$, —$PO(R^o)_2$, —$OPO(R^o)_2$, =O, =S, =$NNHR^o$, =$NN(R^o)_2$, $NNHC(O)R^o$, =$NNHCO_2$($C_{1-6}$ alkyl), =$NNHSO_2(C_{1-6}$alkyl), =NOH, =$NR^o$; or $C_{1-10}$ alkylidene chain, wherein up to three methylene units of the chain are independently replaced by —$NR^o$—, —O—, —S—, —SO—, $SO_2$—, or each $R^3$ and $R^4$ is independently H, halogen, or $C_{1-4}$ aliphatic optionally substituted with 0-5 occurrences of halogen, OH, $OCH_3$, $OCF_3$, $NO_2$, $NH_2$, CN, $NHCH_3$, $SCH_3$, $N(CH_3)_2$, or $C_{1-2}$aliphatic optionally substituted 0-5 times with F;

Q-$Q^1$ is selected from

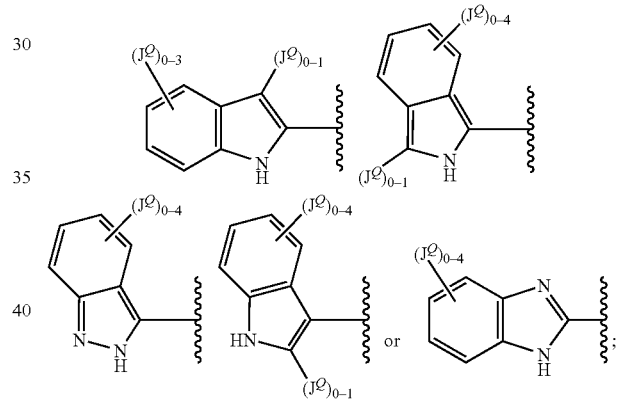

Q-$Q^1$ is substituted with up to 3 $J^Q$ groups wherein each $J^Q$ is independently selected from CN, halo, $C_{1-6}$alkyl, $C_{1-4}$haloalkyl, —$OR^o$, —$N(R^o)_2$, —$SR^o$, —($C_{1-6}$alkyl)-$OR^o$), —($C_{1-6}$alkyl)-$N(R^o)_2$, —($C_{1-6}$alkyl)-$SR^o$, —(U)$_m$—($C_{6-10}$aryl), —(U)$_m$-(5-12 membered heteroaryl), —(U)$_m$-(3-12 membered heterocyclyl), —(U)$_m$—($C_{3-10}$cycloaliphatic), —$C(O)OR^o$, —$NR^o$-$COR^o$, —COPY, —$CON(R^o)_2$, —$SO_2R^o$, and —$SO_2N(R^o)_2$;

U is a $C_{1-10}$alkyl, wherein 0-1 methylene units are independently replaced by, —$NR^o$—, —O—, or —S—;

m is 0 or 1;

each $J^Q$ and $J^{R2}$ is independently and optionally substituted with 0-5 $R^X$;

each $R^X$ is independently H, halogen, $NO_2$, CN, $NH_2$, $NH(C_{1-4}$aliphatic), $N(C_{1-4}$aliphatic)$_2$, OH, $O(C_{1-4}$aliphatic), $O(C_{1-4}$haloaliphatic), $CO(C_{1-4}$aliphatic), $CO_2H$, $CO_2(C_{1-4}$aliphatic), $C_{1-6}$aliphatic, $C_{1-4}$haloaliphatic, phenyl, —O(Ph), 5-6 membered heteroaryl, $C_{3-8}$cycloaliphatic, 5-8 membered heterocyclyl, —$C_{1-6}$aliphatic-(Ph), —$C_{1-6}$alkyl-(5-6 membered heteroaryl), —$C_{1-6}$alkyl-($C_{3-8}$cycloaliphatic), —$C_{1-6}$alkyl- (5-8 membered heterocyclyl), or $C_{1-10}$alkylidene chain wherein up to 2 methylene units of the chain are optionally replaced by O, N, or S; wherein each $R^X$ and is independently and optionally substituted with 0-5 $J^o$;

each $R^o$ is independently H, $C_{1-6}$aliphatic, $C_{1-4}$haloaliphatic, CO($C_{1-4}$aliphatic), CO$_2$($C_{1-4}$aliphatic), —SO$_2$($C_{1-4}$aliphatic), —SO$_2$(phenyl), phenyl, 5-6 membered heteroaryl, 5-8 membered heterocyclyl, $C_{3-8}$cycloaliphatic, —$C_{1-6}$aliphatic-(Ph), —$C_{1-6}$alkyl-(5-6 membered heteroaryl), —$C_{1-6}$alkyl-(5-8 membered heterocyclyl), —$C_{1-6}$alkyl-($C_{3-8}$cycloaliphatic); or $C_{1-10}$alkylidene chain wherein up to 2 methylene units of the chain are optionally replaced by O, N, or S; wherein said $R^o$ is optionally substituted with 0-6 $J^o$;

or two $R^o$, on the same substituent or different substituents, taken together with the atom(s) to which each $R^o$ group is bound, form a 3-8 membered saturated, partially unsaturated, or fully unsaturated monocyclic or bicyclic ring having 0-4 heteroatoms independently selected from nitrogen, oxygen, or sulfur; wherein said ring is optionally and independently substituted with 0-4 occurrences of halogen, NO$_2$, CN, $C_{1-4}$aliphatic, NH$_2$, NH($C_{1-4}$aliphatic), N($C_{1-4}$aliphatic)$_2$, OH, O($C_{1-4}$aliphatic), CO$_2$H, CO$_2$($C_{1-4}$aliphatic), O(halo$C_{1-4}$ aliphatic), or halo$C_{1-4}$aliphatic, wherein each of the $R^oC_{1-4}$ aliphatic groups is unsubstituted;

each $J^o$ is independently halogen, NO$_2$, CN, $C_{1-4}$aliphatic, —NH$_2$, —NH($C_{1-4}$aliphatic), —N($C_{1-4}$ aliphatic)$_2$, —OH, —O($C_{1-4}$aliphatic), —CO$_2$H, —CO$_2$($C_{1-4}$aliphatic), —O(halo$C_{1-4}$ aliphatic), and halo($C_{1-4}$aliphatic), wherein each of the $J^o$ $C_{1-4}$aliphatic groups is unsubstituted.

27. The compound according to claim 26, wherein each $J^Q$ is CN, halo, $C_{1-6}$alkyl, $C_{1-4}$haloalkyl, —OR$^o$, —N(R$^o$)$_2$, —SPY, —NH—($C_{1-6}$alkyl)-(3-8 membered heterocyclyl), —O—($C_{1-6}$alkyl)-(3-8 membered heterocyclyl), 3-8 membered heterocyclyl, —C(O)OR$^o$, —NR$^o$COR$^o$, —COP), —CON(R$^o$)$_2$, —SO$_2$R$^o$, or —SO$_2$N(R$^o$)$_2$; wherein each $J^Q$ is optionally and independently substituted with 0-5 $R^X$.

\* \* \* \* \*